US008666765B2

(12) United States Patent
Zilberman et al.

(10) Patent No.: US 8,666,765 B2
(45) Date of Patent: Mar. 4, 2014

(54) ONLINE HEALTH CARE CONSUMER PORTAL

(75) Inventors: Maxim Zilberman, Churchville, PA (US); Antony L. Kerz, Rocky Hill, CT (US); Rickey Tang, Southwick, MA (US); Kari Brey, Andover, MN (US)

(73) Assignee: Aetna Inc., Hartford, CT (US)

( * ) Notice: Subject to any disclaimer, the term of this patent is extended or adjusted under 35 U.S.C. 154(b) by 1407 days.

(21) Appl. No.: 11/967,474

(22) Filed: Dec. 31, 2007

(65) Prior Publication Data

US 2009/0171692 A1  Jul. 2, 2009

(51) Int. Cl.
*G06Q 50/00* (2012.01)
*G06Q 10/00* (2012.01)
*G06F 3/00* (2006.01)

(52) U.S. Cl.
USPC .................................. 705/2; 705/3; 715/760

(58) Field of Classification Search
USPC ......................................................... 705/2–3
See application file for complete search history.

(56) References Cited

U.S. PATENT DOCUMENTS

| | | | |
|---|---|---|---|
| 6,459,364 B2 | 10/2002 | Gupta | |
| 6,591,008 B1 | 7/2003 | Surve et al. | |
| 6,784,905 B2 | 8/2004 | Brown et al. | |
| 6,824,053 B2 | 11/2004 | Bluemer | |
| 7,188,318 B2 * | 3/2007 | Spisak | 715/827 |
| 7,216,298 B1 * | 5/2007 | Ballard et al. | 715/760 |
| 2006/0061586 A1 | 3/2006 | Brulle-Drews et al. | |
| 2007/0028178 A1 * | 2/2007 | Gibson et al. | 715/760 |
| 2007/0150305 A1 * | 6/2007 | Abraham-Fuchs et al. | 705/2 |
| 2007/0230749 A1 | 10/2007 | Foss | |
| 2007/0250189 A1 | 10/2007 | Rourke et al. | |

* cited by examiner

*Primary Examiner* — Minnah Seoh
(74) *Attorney, Agent, or Firm* — Leydig, Voit & Mayer, Ltd.

(57) ABSTRACT

An online health care consumer portal for accessing one or more health-related services by a health care consumer. The consumer portal includes an authentication module for identifying the health care consumer upon receiving an online identification token, and a database for maintaining health care information comprising a plurality of health records. The consumer portal also includes a rules engine module for applying a set of rules to the one or more health records corresponding to the consumer to determine an impairment profile of the health care consumer based on the health records corresponding to the health care consumer and an online user interface for providing access to the health-related services. The online user interface is configurable from a default configuration to a second configuration upon identification by the authentication module, the second configuration adapted to facilitate use of the online user interface according to the impairment profile.

17 Claims, 5 Drawing Sheets

ONLINE HEALTH CARE CONSUMER PORTAL

BACKGROUND OF THE INVENTION

Consumers use the Internet to access numerous types of health-related information and services. For example, consumers log into insurance company or health care organization websites in order to view available products, apply for products, or utilize one of many services offered by health care organizations. The services offered by health-related organizations include pharmaceutical research and sales, health research, health news, and others.

An online interactive personal health record (PHR) may be accessed by a consumer in order to view, modify, and otherwise interact with the PHR. A consumer's PHR typically holds personal information from numerous sources including the consumer, the consumer's health care providers, and the consumer's health care organization or insurance company. The personal information stored in a PHR often includes information relating to the consumer's prescriptions, over-the-counter medications taken by the consumer, the consumer's health care providers, and appointments scheduled by the consumer.

Health care organizations typically offer online services to consumers and potential consumers. For example, a consumer portal of a health care organization may operate a website that offers the services described above, as well as health insurance-related services such as access to claims data, access to insurance products, services for claim disputes, and other health services.

Often consumers have one or more conditions that impair their ability to use equipment for accessing the Internet. For instance, a consumer with poor eyesight may not be able to read text on a webpage. A colorblind consumer may have trouble viewing the webpage depending on the colors used. Consumers may have impaired motor skills, perhaps from a disease such as Parkinson's, which makes it difficult to interact with a webpage by, for example, clicking buttons, selecting checkboxes or radio buttons, entering text, or clicking links. In general, there is a wide variety of conditions which can make it difficult for certain consumers to utilize web pages.

BRIEF SUMMARY OF THE INVENTION

The invention provides an online health consumer portal for accessing one or more health-related services by a health care consumer. The consumer portal includes an authentication module for performing identification of the health care consumer upon receiving an online identification token from the health care consumer. A database of health records, one or more of which correspond to the health care consumer, is maintained. The consumer portal includes a rules engine module for applying a set of rules to the health records corresponding to the health care consumer in order to determine an impairment profile of the health care consumer based on the health care consumer's health records. The consumer portal also includes an online user interface for providing access to the health-related services. The online interface is configurable from a default configuration to a second configuration upon identification by the authentication module. In the second configuration, the user interface is adapted to facilitate use of the online user interface by the health care consumer according to the impairment profile.

A method of operating a health care consumer portal for accessing one or more health related services is provided in accordance with another embodiment. The method includes providing an online user interface over a communications network, the online user interface for accessing the health-related services. The method also includes receiving an online identification token from a health care consumer over the communications network. A set of rules is applied to one or more health records relating to the health care consumer to determine an impairment profile of the health care consumer. The one or more health records come from a database comprising a plurality of health records. The online user interface is adjusted according to the impairment profile in order to facilitate use of the online user interface by the user.

A computer readable medium having stored thereon computer executable instructions for operating a health care consumer portal, the portal for accessing one or more health-related services, is provided in accordance with yet another embodiment. The consumer portal provides an online user interface over a communications network, the online user interface for accessing the health-related services. The consumer portal receives an online identification token from a health care consumer over the communications network. A set of rules is applied to one or more health records relating to the health care consumer to determine an impairment profile of the health care consumer. The one or more health records are from a database comprising a plurality of health records. The online user interface is adjusted according to the impairment profile in order to facilitate use of the online user interface by the user.

DETAILED DESCRIPTION OF THE INVENTION

Figure 1:
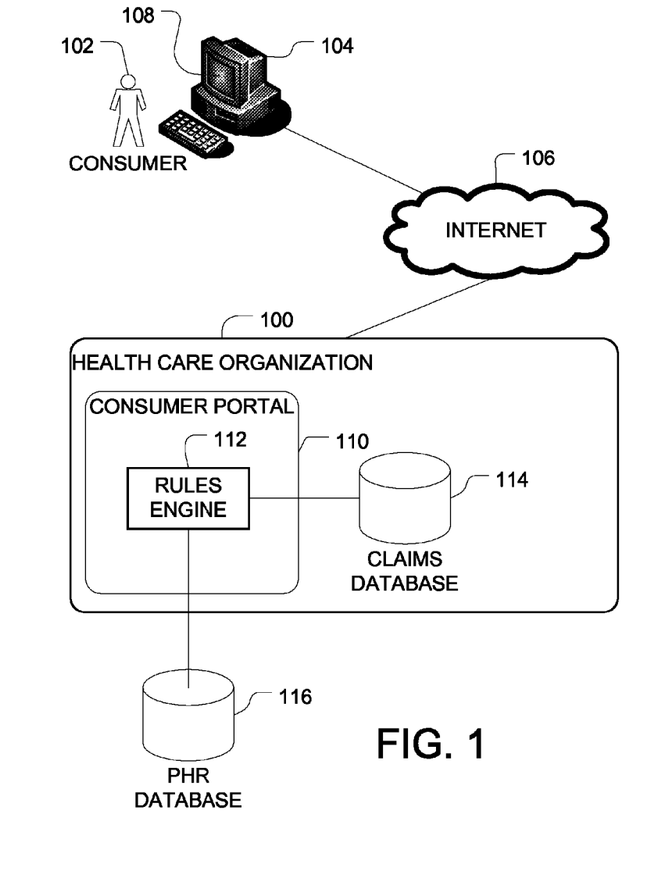
FIG. 1 shows a diagram of a system for operating an online health care consumer portal, in accordance with an embodiment.

FIG. 1 shows representation of a system operated by a health care organization 100, in accordance with an embodiment. As shown in the drawing, a health care consumer 102 uses a personal computer 104 to connect to a website of the health care organization 100 via the Internet 106. In particular, a user interface 108 appears on a screen of the personal computer 104 according to instructions sent via the Internet 106 of an internet server of the health care organization 100. Alternatively, the user interface 108 can appear on any device capable of accessing the Internet, such as a personal digital assistant or a cellular telephone.

The user interface 108 is a visual representation of a consumer portal 110 operated by the health care organization 100. In an embodiment, the user interface 108 includes text, pictures, and other media appearing on the screen of the personal computer 104. The user interface 108 also includes navigation controls for allowing the health care consumer 102 to navigate to different areas of the consumer portal 110, and other controls, such as controls commonly found in web pages such as links, text boxes, radio buttons, and checkboxes.

The consumer portal 110 includes a rules engine 112 which interacts with an internal claims database 114 and an external PHR database 116. As described more fully below, the rules engine 112, in an embodiment, retrieves information related to the health care consumer 102 from the internal claims database 114 and external PHR database 116 and, from that information, infers whether there is a likelihood that a health care consumer 102 has a health condition which impairs his or her use of devices for connecting to the consumer portal 110.

In accordance with an embodiment, the claims database 114 includes data records corresponding to insurance claims made by the health care consumer 102. For example, the claims database 114 contains records relating to claims made by the health care consumer 102 for medical treatments, diagnostic procedures, medical devices, and prescription medicine. The PHR database 116 includes records relating to the health care consumer 102 which are created by the health care consumer 102, or are input by third-parties, such as medical providers of the health care consumer 102. For instance, the PHR database includes summaries of the health care consumer's 102 health and medical history, which was entered into the PHR database 116 by the health care consumer 102 himself or herself or by another party, such as physician of the health care consumer 102.

In an embodiment, either or both of the claims database 114 and PHR database 116 include other records relating to the health care consumer 102 such as records from an integrated voice response system, which is an automated system for accepting telephone-originated user requests for claim status, account administration, and the like; records relating to disease management call input, which is a health care organization application where a clinician or nurse interacts with a patient to manage a chronic disease, discuss treatment progress, and manage medications taken in connection with the disease; and electronic medical record information, where an electronic medical record (EMR) application is used by doctors or other health care professionals at their place of business, such as a clinic, to enter patient data related to the patient's treatment and diagnosis, such as information relating to performed medical procedures, issued prescriptions, and the like. In an embodiment, the PHR database 116 interacts with a PHR system which analyzes data in order to interact with the consumer to assist him or her with maintaining his or her health. For instance, the PHR system reviews medications taken by the consumer and alerts him or her of potential drug interactions. The PHR system reminds the consumer of appointments with health care providers, and provides other reminders, such as a reminder to schedule an annual physical with a primary care physician.

Figure 2:
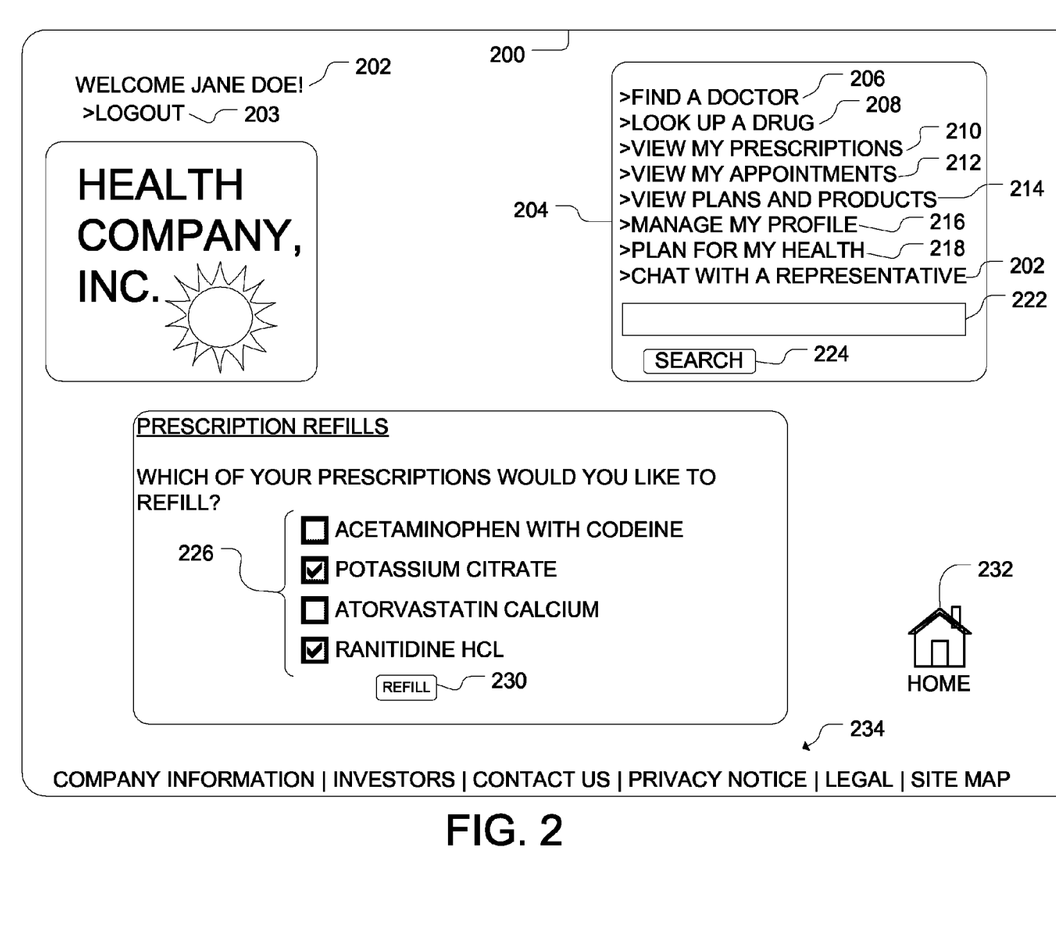
FIG. 2 shows a diagram of a default interface page of the online health care consumer portal of FIG. 1.

FIG. 2 shows a diagram of a default interface page 200 of the consumer portal 110 which, in accordance with an embodiment, is displayed by a web browser to the health care consumer 102 on a screen of the personal computer 104. The default interface page 200 is displayed in a default configuration, which is the configuration displayed to health care consumers who do not have a condition impairing their ability to interact with the user interface 108. The default interface page 200 includes several features for viewing information and navigating to other pages in order to access services of the consumer portal 110.

In the example shown in FIG. 2, the default interface page 200 includes an indicator 202 that a health care consumer 102 is logged in and recognized by the consumer portal 110. The default interface page 200 includes a logout link 203 for allowing a logged in health care consumer to exit the consumer portal 110, perhaps for security purposes so that subsequent users will not be able to access personal information of the health care consumer 102.

In an embodiment, the default interface page 200 includes a variety of user services 204. As shown in FIG. 2, the user services 204 include a link 206 to a page for finding contact information for a doctor and a link 208 to a page for researching drug information. The user services 204 also include services personalized to the health care consumer 102 such as a link 210 for viewing prescriptions of the health care consumer 102, a link 212 for viewing appointments of the health care consumer 102, and a link 214 for viewing plans and products purchased by the health care consumer 102. In an embodiment, a link 216 is provided for managing the consumer's profile, the profile including specific information about the health care consumer 102, such as contact information, and a link 218 is provided for health care planning. A link 220 can be selected by the health care consumer 102 in order engage in an online chat session with a representative of the health care organization 100, perhaps if the health care consumer 102 needs technical assistance navigating the consumer portal 102 or assistance with products and services.

In an embodiment, a search box 222 along with a search button 224 is included, the search button being selectable by the health care consumer 102 for searching for documents containing terms entered in the search box 222. The interface also includes a frame, window, or area of the screen or the personal computer 104 containing information specific to a particular area of the consumer portal 110 currently accessed by the health care consumer 102. For example, in the example shown in FIG. 2, the default interface page 200 includes a series of checkboxes 226, each checkbox displaying the name of prescription drug to which the health care consumer 102 currently has a prescription. A refill button 230 is provided for selection by the health care consumer 102 in order to direct the consumer portal 110 to order refills of the prescriptions indicated by the health care consumer 102 by checking one or more of the checkboxes 226.

Other features are also included, such as a link 232 for returning to a home page of the consumer portal 110 which, in an embodiment, shows an icon of a house over the word "HOME" indicating that the health care consumer 102 may select the house icon in order to navigate to a start page of the consumer portal 110. A list 234 of links for navigating to commonly accessed pages of the consumer portal 110 is included at the bottom of the default interface page 200.

Figure 3:
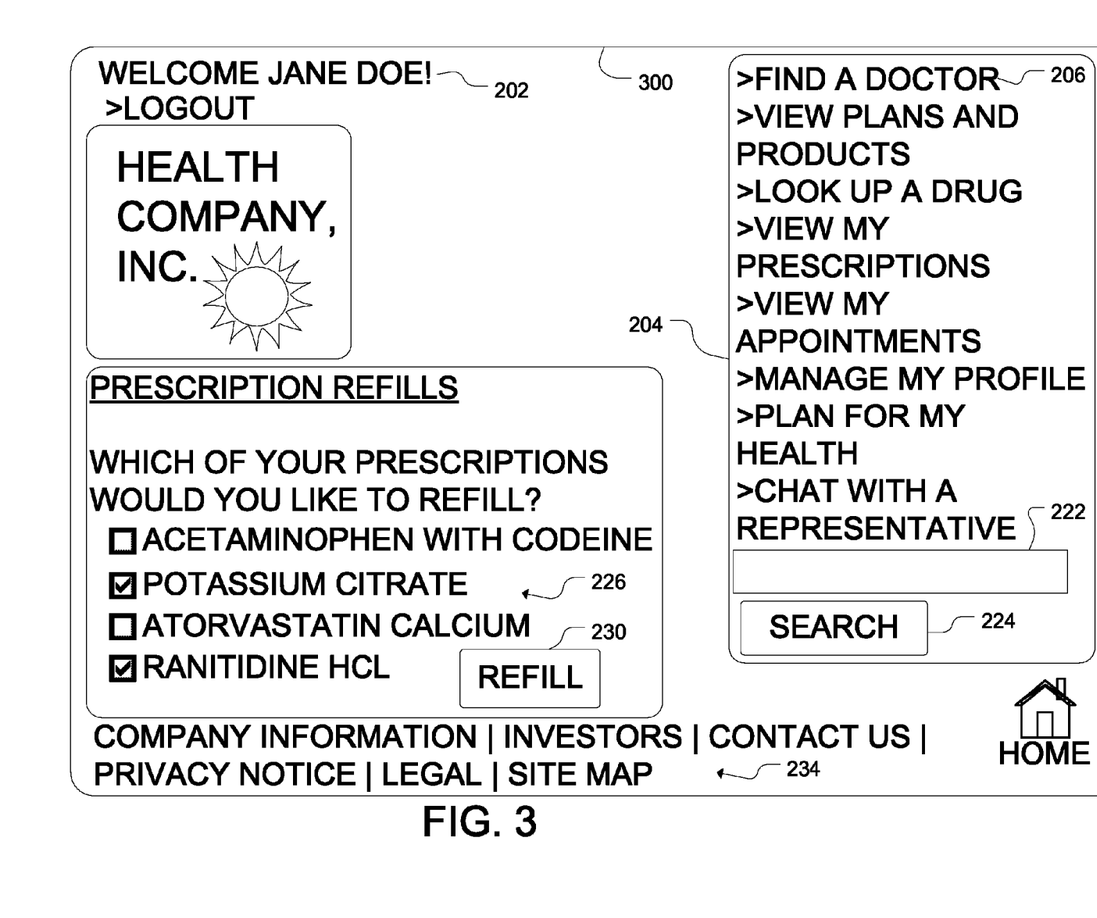
FIG. 3 shows the interface page of FIG. 2 adapted for use by severely visually impaired health care consumers.

FIG. 3 shows an interface page 300 which, in an embodiment, is the default interface page 200 shown in FIG. 2 adapted for use by a health care consumer 102 having severe visual impairment. In an embodiment, text appearing on the interface page 300 appears in a larger font size than on the default interface page 200. For example, the text of the indicator 202 appears in a larger font size than on the default interface page 200. A larger font size for text identifying the user services 204 is also used. For instance, the link 206 for finding a doctor appears larger than in the default interface page 200.

Other features of the default interface page 200 are also enlarged for severely visually impaired consumers. In an embodiment, the search bar 222 and the search button 224 are enlarged compared to their size on the default interface page 200. In addition, the checkboxes 226 along with their text and the refill button 230 are also enlarged as are the links 234 provided at the bottom of the default interface page 200.

Other mechanisms for facilitating use of the consumer portal 110 for severely visually impaired consumers are also employed, in an embodiment. As an example, different colors than those used on the default interface page 200 are used on the interface page 300 for severely visually impaired consumers, the colors used in the interface page 300 chosen to facilitate perception by a person with severe visual impairment. In addition, in an embodiment, the contrast between adjacent colors is increased. As another example, in an embodiment, an Internet browser viewing the default interface page 300 may direct the personal computer 104 of the health care consumer 102 to play audio corresponding to text underneath the location of an on-screen pointer whose movement is determined by a mouse or other input device connected to the personal computer 104. Thus, if the health care consumer 102 places the pointer over the link 206 is for finding a doctor, the personal computer 104 plays a digital recording of a voice saying "find a doctor" so that the health care consumer 102 can recognize or confirm that the link 206 for finding a doctor. As yet another example, some or all of the text in the interface page 300 can appear in a different font than on the default interface page 200. In general, any mechanism or feature for assisting a severely impaired consumer to navigate a website can be employed on the interface page 300 for severely visually impaired consumers in combination with or as an alternative to those described above. Additionally, while FIG. 3 shows the features of the default interface page 200 enlarged, but laid out in a manner so as to fit on one screen, adapting the user interface 108 for severely impaired consumers or for consumers having other conditions can include more drastic layout changes or introducing a completely different interface.

Figure 4:
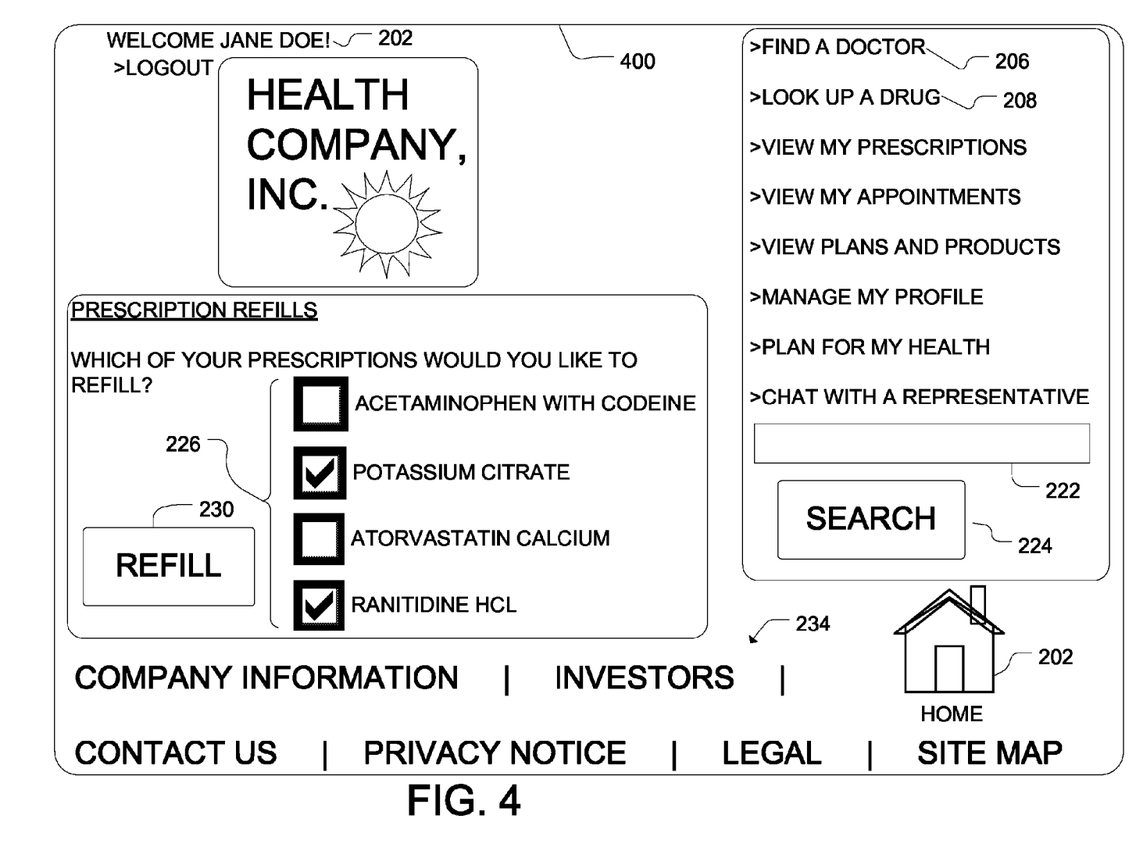
FIG. 4 shows the interface page of FIG. 2 adapted for use by health care consumers having impaired motor skills.

FIG. 4 shows an interface page 400 of the consumer portal 110 which, in an embodiment, is the default interface page 200 adapted for use by a consumer having impaired motor skills such as a health care consumer 102 having Parkinson's disease. As shown in FIG. 4, the interface page 400, in an embodiment, includes the same features as the default interface page 200; however, the features shown in the interface page 400 are presented differently than on the default interface page 200. Specifically, the user services 204 are spaced further apart in the interface page 400 than on the default interface page 200. As shown in FIG. 4, for example, the link 206 for finding a doctor and the link 208 for researching drug information have greater space between one another than on the default interface page 200. A user can select the link 206 for finding a doctor by placing an on-screen pointer in the general vicinity of the link 206 for finding a doctor and clicking a mouse of the personal computer 104, or otherwise selecting the link using another input device. Because of the separation between the link 206 for finding a doctor and the link 208 for researching drugs, it is less likely that a consumer with impaired motor skills will select one link while intending to select the other.

Other features of the default interface page 200 adapted for use by consumers with impaired motor skills in the interface page 400 include a larger search box 222 and a larger search button 224 which make it easier to place a cursor in the search box 22 in order to enter text and subsequently select the search button 224 to conduct a search. Likewise, the checkboxes 226 are increased in size to enable a health care consumer with impaired motor skills to more easily select his or her prescriptions which he or she would like to refill by selecting the refill button 230 which is also of larger size when compared to its size in the default interface page 200. In an embodiment, other selectable features are enlarged and separated to reduce the likelihood that one feature will be selected while another was intended. For example, the set of common links at the bottom of the default interface page 200 appear larger in two rows instead of one and with greater horizontal separation in the interface page 400 shown in FIG. 2.

Additional or alternative features and mechanisms for facilitating use of the consumer portal 110 by persons having impaired motor skills can be incorporated into the interface page 400 in addition to or as an alternative to those described above. In general, the default interface page 200, and any page of the consumer portal 110 can be adapted to facilitate use of the consumer portal 110 by a user having any condition impairing use of the consumer portal 110. For example, if the health care consumer 102 has a specific colorblindness condition, the consumer portal 110 can adjust the colors displayed on the default page 200 to avoid problematic color combinations that may impair viewing by the health care consumer 102. Subtitles or other text can accompany any content of the consumer portal 110 containing audio in order to facilitate use by health care consumers having full or partial hearing impairment. The default interface page 100 can also be adapted to assist in use of the consumer portal 110 by a person having more than one condition impairing use of the consumer portal 110 by combining features and mechanisms designed to facilitate use of the consumer portal 110 according to each condition. For example, if the health care consumer 102 has both impaired motor skills and severe visual impairment, the font size of text may be increased (to aid in reading the text) and selectable links and other navigation tools may be increased in size (to aid both in seeing the links and navigation tools and ease selection by the user). If the health care consumer 102 is additionally colorblind, the colors appearing on the default page 200 can be adjusted to avoid color combinations impairing perception of the user interface 108.

In accordance with an embodiment, adjusting the user interface 108 also includes other actions for facilitating use by the health care consumer 102. For instance, the consumer portal 110 sends instructions to the personal computer 104 for the personal computer 104 to modify its behavior, such as by instructing the personal computer 104 to increase the size of the on-screen pointer, to modify settings of an Internet browser used by the personal computer 104 to view the user interface 108, or changing other setting of the personal computer 104. Additionally, while the examples shown in FIGS. 3 and 4 show the default interface page 200 adapted in a manner such that the overall layout and design of the default interface page 200 is preserved, adapting the user interface 108 can also include making more drastic changes that do not necessarily preserve the layout and design of the default interface page 200. Adapting the user interface 108, in an embodiment, also includes varying the adaptation based on the severity of impairment of the health care consumer 102.

Figure 5:
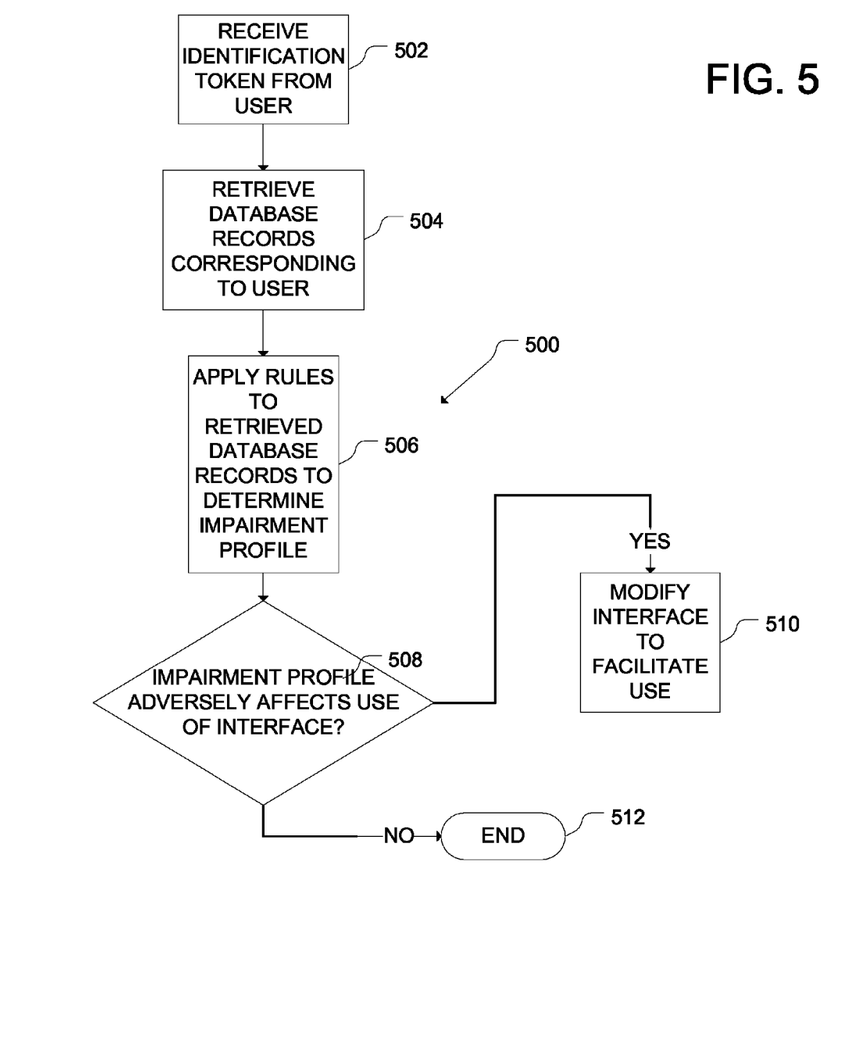
FIG. 5 shows a procedural flow chart for operating the online consumer portal of FIG. 1.

FIG. 5 shows a procedural flow chart 500 for operating the consumer portal 110 in accordance with an embodiment. The consumer portal at step 502 receives an identification token from the health care consumer 102. The step 502 is encoded in an authentication module and performed by a computer, server, or other machine capable of processing instructions, where a module is a computer readable medium, database, or memory storing instructions to be processed by the computer, server, or other machine. An identification token is a piece of information unique to the health care consumer 102 or relating to or identifying the health care consumer 102. In an embodiment, the identification token includes a user name and a password, with the user name comprising a unique identifier of the health care consumer 102 and the password being a string of characters chosen by the health care consumer 102 for accessing services and information of the consumer portal 110 specific to him or her.

In an alternate embodiment, the identification token is a Hypertext Markup Language (HTML) cookie stored on the personal computer 104 of the health care consumer 102. For instance, if the health care consumer 102 accesses the consumer portal 110 by entering a user name and password, an Internet server of the health care organization 100 sends a cookie to the personal computer 104 of the health care consumer 102 over the Internet 106 in order to identify the personal computer 104 of the health care consumer 102. The next time the health care consumer 102 uses the personal computer 104 to submit a request over the Internet 106 to access the consumer portal 110, the personal computer 104 sends the cookie over the Internet 106 to the consumer portal 110 so as to identify itself to the consumer portal 110.

In yet another embodiment, the identification token comprises biometric or other data submitted by the health care consumer 102 over the Internet 106 to the consumer portal 110. For example, a thumbprint reader can be connected to the personal computer 104 so that the health care consumer 102 can send a digital representation of a thumbprint over the Internet 106 to the consumer portal 110 which in turn would recognize the thumbprint as belonging to the health care consumer 102. Biometric data may also include retinal images, voice recordings, digital images, or other data derived from unique biological features of the health care consumer 102. Other mechanisms for submitting identification tokens by the health care consumer 102 to the consumer portal 110 can also be used, such as a radio frequency identification (RFID) tag of the health care consumer 102 and read by a device connected to the personal computer 104 for receiving a signal from the RFID tag.

Upon receiving the identification token from the health care consumer 102 and authenticating the health care consumer 102, the consumer portal 110, at step 504, retrieves database records corresponding to the health care consumer 102 from the claims database 114 and PHR database 116. During step 504, in an embodiment, the consumer portal 110 uses information from the identification token to match data records to the health care consumer 102.

Once the database records have been retrieved, the consumer portal 110 applies a set of rules to the database records to determine an impairment profile at step 506. In an embodiment, the step 506 for applying the set of rules to the database records is encoded in a rules engine module. Application of rules to the database records, in an embodiment, include employment of a rules engine such as the Care Engine System disclosed in U.S. application Ser. No. 11/749,654, which is incorporated herein by reference for everything that it teaches.

An impairment profile is a piece of information indicating whether the health care consumer 102 has one or more conditions which possibly impair his or her use of the consumer portal 110. In an embodiment, the impairment profile comprises a list of one or more conditions the health care consumer 102 possibly has which may impair his or her use of the consumer portal 110. The impairment profile can also include other information such as a unique identifier of the health care consumer 102 in order to enable storing the impairment profile in a data store for subsequent retrieval. In another embodiment, the impairment profile has, for each condition listed in the impairment profile, an indicator of the probability that the health care consumer 102 has the condition for each of the conditions listed in the impairment profile. The probability can be assigned by the rules engine so as to approximate actual probabilities as determined by research data or other sources so as to indicate a confidence level of the consumer portal 110 that the consumer 102 has a condition. Thus, if the claims data in the claims database 114 showed a claim for a drug which, according to research, is used 80% of the time to treat Parkinson's, the probability in the impairment profile corresponding to Parkinson's would be at least 0.8 absent other data indicating that the drug is used for another purpose. In an another embodiment, the impairment profile includes, for each condition listed in the impairment profile, a data value corresponding to the severity of the condition so that adjustment of the user interface 108 is partially determined by the severity of the condition. Thus, for example, the font size displayed to the health care consumer 102 depends on the severity of visual impairment.

As an example of how the consumer portal 110 applies rules to database records to determine an impairment profile, if the claims database 114 includes a record that the health care consumer 102 made a claim for a prescription for pramipexole, commonly used to treat Parkinson's (with which impaired motor skills is a symptom and which is treated by a neurologist) but also used to treat fibromyalgia (which generally does not involve impaired motor skills and is generally not treated by a neurologist, but a rheumatologist), and a claim for treatment by a neurologist, the rules engine would determine that the combination of claims indicates that the health care consumer 102 possibly has Parkinson's, which would be noted in the impairment profile of the health care consumer 102. If the claims database 114 includes a record of a claim for pramipexole and a claim for treatment by a rheumatologist, but no claims for treatment by a neurologist, the rules engine would not determine that the health care consumer 102 has Parkinson's or, in an alternate embodiment, the rules engine would determine that the health care consumer possibly has Parkinson's, but would assign a lower probability to the possibility than if there had been claims for treatment by a neurologist. Therefore, the rules engine infers that the health care consumer 102 possibly has a condition impairing use of the user interface 108 by using multiple pieces of data when one piece of data does not have enough information to make such a determination. The rules engine refines its determination that the health care consumer 102 has a condition impairing use of the user interface 108 by using multiple data records.

As another example of how the rules engine applies rules to database records to determine an impairment profile, if any claim of the health care consumer 102 in the claims database 114 contains a diagnosis code, such as an ICD-9 diagnosis code, that indicates the possibility of severe visual impairment, than the consumer portal 110 would include the possibility of severe visual impairment in the impairment profile for the health care consumer 102. Likewise, if data in the PHR database 116 contains data that indicates severe visual impairment, such as input by the health care consumer 102 that he or she has severe visual impairment, than the consumer portal 110 would include the possibility of severe visual impairment in the impairment profile for the health care consumer 102.

While the step 506 of applying the rules engine to data in a database to determine an impairment profile can be completed every time the consumer portal receives an identification token from the health care consumer 102, it may be done less frequently. For instance, in an embodiment, the step 506 is completed the first time the consumer portal 110 receives an identification token from the health care consumer 102 and the impairment profile is stored in a data store for later retrieval at a later time upon a subsequent receipt of an identification token from the health care consumer 102. In another embodiment, the step 506 is completed the first time the consumer portal 110 receives an identification token from the health care consumer 102 and the impairment profile is stored in a data store for later retrieval. At a later time, when the consumer portal 110 receives an identification token from the health care consumer 102, the consumer portal 110 retrieves the identification token from the data store and applies the rules engine to any new data in the databases 114, 116 to which the rules engine has not been applied and modifies the impairment profile according to the result of applying the rules engine to the new data. In this instance, the rules engine can also be re-applied to a selection of relevant records of the databases 114, 116, such as records relating to any impairing conditions indicated in the new data.

Once the impairment profile is determined, the consumer portal 110 determines whether the impairment profile indicates the possibility of a condition impairing use of the user interface 108 at step 508. If the consumer portal 110 at step 508 determines that the impairment profile does adversely affect use of the user interface 108, the consumer portal 110 modifies the user interface 108 to facilitate use of the user interface 108 according to the impairment profile at step 510. For example, in an embodiment, if the impairment profile shows that the health care consumer 102 possibly has Parkinson's, the consumer portal 110 will display the user interface 108 using larger selectable features such as those described in connection with FIG. 4. Likewise, if the impairment profile indicates that the health care consumer 102 is possibly severely visually impaired, the consumer portal 110 displays the user interface 108 using larger fonts, different fonts, different colors, larger selectable features, or any other mechanism such as those described in connection with FIG. 3. If the impairment profile indicates that the health care consumer 102 possibly has both Parkinson's and severe visual impairment, the consumer portal 110 displays the user interface 108 to the health care consumer 102 by combining changes made for consumers having Parkinson's and for consumers having severe visual impairment, for example by combining the display of features described in connection with FIGS. 3 and 4.

In an alternate embodiment, at step 510, if the consumer portal 110 determines that the impairment profile indicates the possibility of a condition impairing use of the consumer portal 110 at step 508, the consumer portal 110 displays a choice to the health care consumer 102 whether to use the default interface or an alternate interface designed for facilitating use of the consumer portal 110 for those having the condition. The choice displayed by the consumer portal 110 can be in a form designed for use by users having the condition, can be in a form similar to the form of the default interface 200, or can be presented in both forms.

If the consumer portal 110 at step 508 determines that the impairment profile does not indicate a condition impairing use of the consumer portal 110, the consumer portal 110 at step 512 displays a default interface to the health care consumer 102.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An online health care consumer portal for accessing one or more health-related services by a health care consumer, the portal comprising:
   an authentication module configured to identify the health care consumer upon receiving an online identification token from the health care consumer;
   a database configured to maintain health care information, the database comprising a plurality of health records, one or more of the plurality of health records corresponding to the health care consumer;
   a rules engine module configured to: (a) access the one or more of the plurality of health records corresponding to the health care consumer from the database, (b) apply a set of rules to the one or more health records corresponding to the health care consumer to determine a health impairment profile of the health care consumer by determining based on the one or more of the plurality of health records that the health care consumer has a health condition that impairs the health care consumer's use of the portal, and (c) without user intervention, modify an online user interface of the portal so as to compensate for the health condition associated with the health impairment profile ; and
   the online user interface configured to provide access to the one or more health-related services, the online user interface configurable, without user intervention, from a default configuration to a second configuration upon identification by the authentication module of the consumer corresponding to the health impairment profile, the second configuration adapted to facilitate use of the online user interface by the health care consumer according to the health impairment profile.

2. The online health care consumer portal of claim 1, wherein the health impairment profile indicates one or more possible health conditions of the health care consumer, the one or more possible health conditions selected from the group consisting of a visual impairment, a motor skills impairment, a hearing impairment, and colorblindness.

3. The online health care consumer portal of claim 1, wherein the database comprises information from at least one source selected from the group consisting of an online personal health record database, an electronic medical record, a disease management call, and an integrated voice response system.

4. The online health care consumer portal of claim 1, wherein the second configuration facilitates use of the online user interface by the health care consumer by modifying at least one user interface element, the at least one user interface element selected from the group consisting of text size, radio button size, check box size, separation between navigation controls, color contrast, color scheme, font type, text content, and audio content.

5. The online health care consumer portal of claim 1, wherein the online user interface presents the health care consumer with a choice of using the default configuration or the second configuration upon determination of the health impairment profile.

6. A method of operating a health care consumer portal for providing one or more health-related services, the method comprising:
providing, via a computer server system, an online user interface for accessing the one or more health-related services over a communications network;
receiving, via the computer server system, an online identification token from a health care consumer over the communications network;
in response to receiving the online identification token:
(a) accessing one or more health records relating to the health care consumer;
(b) applying a set of rules to the one or more health records relating to the health care consumer to determine a health impairment profile of the health care consumer by determining based on the one or more health records that the health care consumer has a health condition that impairs the health care consumer's use of the portal; and
(c) configuring, without user intervention, via the computer server system, the online user interface adapted to compensate for the health condition associated with the health impairment profile in order to facilitate use of the online user interface by the health care consumer.

7. The method of claim 6, wherein the health impairment profile indicates one or more possible health conditions of the health care consumer, the one or more possible health conditions selected from the group consisting of a visual impairment, a motor skills impairment, a hearing impairment, and colorblindness.

8. The method of claim 6, wherein the database comprises information from at least one source selected from the group consisting of an online personal health record database, an electronic medical record, a disease management call, and an integrated voice response system.

9. The method of claim 6, wherein the step of configuring the online interface includes one or more steps selected from the group consisting of increasing text size, increasing radio button size, increasing check box size, increasing separation between navigation controls, increasing contrast, modifying a color scheme, modifying font type, displaying subtitles associated with an audio broadcast, and providing an audio version of text.

10. The method of claim 6, further comprising receiving a choice from the health care consumer to adjust the online user interface according to the impairment profile.

11. The method of claim 6, wherein configuring the online user interface comprises sending instructions to a device of the health care consumer for connecting to the Internet, the instructions modifying behavior of the device.

12. A non-transitory computer readable medium having stored thereon computer executable instructions for operating a health care consumer portal, the portal providing one or more health-related services, the instructions comprising:
providing an online user interface for accessing the one or more health-related services over a communications network;
receiving an online identification token from a health care consumer over the communications network;
in response to receiving the online identification token:
(a) accessing one or more health records relating to the health care consumer;
(b) applying a set of rules to the one or more health records relating to the health care consumer to determine a health impairment profile of the health care consumer by determining based on the one or more health records that the health care consumer has a health condition that impairs the health care consumer's use of the portal; and
(c) configuring, without user intervention, the online user interface adapted to compensate for the health condition associated with the health impairment profile in order to facilitate use of the online user interface by the health care consumer.

13. The computer readable medium of claim 12, wherein the health impairment profile indicates one or more possible health conditions of the health care consumer, the one or more possible health conditions selected from the group consisting of a visual impairment, a motor skills impairment, a hearing impairment, and colorblindness.

14. The computer readable medium of claim 12, wherein the database comprises information from at least one source selected from the group consisting of an online personal health record database, an electronic medical record, a disease management call, and an integrated voice response system.

15. The computer readable medium of claim 12, wherein the instructions for configuring the online interface further comprise one or more instructions selected from the group consisting of increasing text size, increasing radio button size, increasing check box size, increasing separation between navigation controls, increasing contrast, modifying a color scheme, modifying font type, displaying subtitles associated with an audio broadcast, and providing an audio version of text.

16. The computer readable medium of claim 12, wherein the instructions further comprise receiving a choice from the health care consumer to adjust the online user interface according to the impairment profile.

17. The computer readable medium of claim 12, wherein the instructions for configuring the online user interface further comprise sending instructions to a device of the health care consumer for connecting to the Internet, the instructions modifying behavior of the device.

* * * * *